US010349841B2

(12) United States Patent
Li

(10) Patent No.: US 10,349,841 B2
(45) Date of Patent: Jul. 16, 2019

(54) BLOOD PRESSURE CUFF ASSEMBLY FOR AMBULATORY BLOOD PRESSURE MONITOR

(71) Applicant: XI'AN SHEN MINDRAY MEDICAL ELECTRONICS RESEARCH INSTITUTE CO., LTD., Shanxi (CN)

(72) Inventor: Guang Li, Shenzhen (CN)

(73) Assignee: XI'AN SHEN MINDRAY MEDICAL ELECTRONICS RESEARCH INSTITUTE CO., LTD., Xi'an (CN)

( * ) Notice: Subject to any disclaimer, the term of this patent is extended or adjusted under 35 U.S.C. 154(b) by 399 days.

(21) Appl. No.: 15/212,108

(22) Filed: Jul. 15, 2016

(65) Prior Publication Data

US 2017/0231512 A1 Aug. 17, 2017

Related U.S. Application Data

(63) Continuation of application No. PCT/CN2014/070552, filed on Jan. 14, 2014.

(51) Int. Cl.
*A61B 5/022* (2006.01)
*A61B 5/021* (2006.01)

(52) U.S. Cl.
CPC .......... *A61B 5/02233* (2013.01); *A61B 5/022* (2013.01); *A61B 5/02141* (2013.01)

(58) Field of Classification Search
CPC .. A61B 5/02233; A61B 5/022; A61B 5/02141
See application file for complete search history.

(56) References Cited

U.S. PATENT DOCUMENTS

| 5,690,672 | A | 11/1997 | Cohen | |
|---|---|---|---|---|
| 6,364,843 | B1 * | 4/2002 | Lightle | A61B 5/02233 600/490 |
| 6,988,992 | B2 * | 1/2006 | Just | A61B 5/02233 600/485 |
| 2008/0236596 | A1 * | 10/2008 | Pierskalla | A61B 5/02233 128/846 |
| 2010/0186752 | A1 | 7/2010 | Rixson | |
| 2013/0165803 | A1 * | 6/2013 | Hung | A61B 5/02233 600/499 |

FOREIGN PATENT DOCUMENTS

| CN | 201404214 Y | 2/2010 |
|---|---|---|
| CN | 203290893 U | 11/2013 |

* cited by examiner

*Primary Examiner* — Christian Jang
*Assistant Examiner* — Karen E Toth
(74) *Attorney, Agent, or Firm* — Kory D. Christensen

(57) ABSTRACT

A blood pressure cuff assembly for an ambulatory blood pressure monitor may include a hollow cuff and an elastic liner provided on the reverse side of the cuff. An airbag may be provided in the cuff. A first connection part and a second connection part may be provided on the cuff. A third connection part and a fourth connection part may be correspondingly provided on the liner. The effect of tight inside and loose outside is achieved by the combination of the elastic liner and the cuff. When worn on an upper arm, the elastic liner has an elastic deformation and consequently tightens around the upper arm so as to realize certain slip resistance, and the cuff will not slip down even tied a bit loosely when located on the upper arm. The feeling of constraint from the cuff is reduced significantly and the comfort is improved.

14 Claims, 9 Drawing Sheets

BLOOD PRESSURE CUFF ASSEMBLY FOR AMBULATORY BLOOD PRESSURE MONITOR

TECHNICAL FIELD

The present disclosure relates to a blood pressure cuff for an ambulatory blood pressure monitor.

BACKGROUND

Ambulatory blood pressure monitoring (ABPM) includes measuring blood pressure at a certain time interval, generally 20 to 30 minutes, by using a blood pressure measuring and recording device for continuous observation for 24 hours to understand a dynamic change of the blood pressure under different physiological states.

ABPM can be used for diagnosing hypertension, determining and evaluating white coat hypertension (WCH) and resistant hypertension (RH), measuring paroxysmal hypertension, assisting in detection of secondary hypertension, evaluating curative effects of antihypertensive drugs, guiding treatment, etc. In some countries, ambulatory blood pressure is already a gold standard for diagnosing hypertension.

An ambulatory blood pressure monitor is a frequently-used tool and an effective approach for monitoring ambulatory blood pressure. Generally, a patient may wear the ambulatory blood pressure monitor in a hospital after a doctor issues an ambulatory blood pressure test list. Then the patient can lead a normal life, work, rest, and return to the hospital after 24 hours for reading test data. An ambulatory blood pressure test report is sent from the hospital, and finally, the doctor gives a diagnostic conclusion.

The ambulatory blood pressure monitor obtains the ambulatory blood pressure of the patient by using an indirect method, which uses a cuff applied to a patient's upper arm for intermittent automatic inflation and pressurization, then picks up a pressure wave signal in an airbag, and measures the blood pressure once every 15 to 30 minutes.

Because the patient is required to continuously wear the ambulatory blood pressure monitor for more than 24 hours during measurement and a blood pressure cuff will be coupled to the upper arm of the patient for long, comfort is of the utmost importance.

The existing cuff embodiments for ambulatory blood pressure monitoring h the following disadvantages:

1) The cuff is required to be fastened to the upper arm of the patient for long periods of time, and must be fastened tightly. If the cuff is fastened too loosely, the cuff may fall or shift, leading to inaccurate blood pressure measurement or failure to measure at all. However, when coupled too tightly, the cuff causes poor blood circulation of the arm and a strong feeling of restraint on the upper arm of the patient. Generally after 24 hours, when the cuff is removed from the body of the patient, the upper arm of the patient may have swelling, bruising, and/or extravasated blood.

2) The cuff is required to be fastened to the upper arm for long periods of time, causing poor permeability and causing the cuff to be dirty and odorous due to perspiration.

3) Because the same monitor is worn by many patients and the same cuff is worn by many people, cross infection of dermatopathy, etc. may occur.

SUMMARY

The present disclosure provides a new blood pressure cuff.

The present disclosure provides a blood pressure cuff which comprises a cuff and an elastic liner. The liner is connected to the reverse side of the cuff. When worn, the liner and the cuff wind and/or cover a target position and the liner is tight and the cuff is loose.

A blood pressure cuff for an ambulatory blood pressure monitor comprises a hollow cuff and an elastic liner provided on the reverse side of the cuff, wherein an airbag is provided in the cuff, a first connection part and a second connection part are provided on the cuff, a third connection part and a fourth connection part are correspondingly provided on the liner, the first connection part is connected with the third connection part, the second connection part is connected with the fourth connection part, the part of the liner between the third connection part and the fourth connection part is straight, and the part of the cuff between the first connection part and the second connection part is arched. When worn, the cuff and the liner wind a target position; the liner has an elastic deformation and consequently tightens around the target position; and the cuff is loose.

A pull ring, a first fixed part and a second fixed part are arranged on the front side of the cuff; the pull ring and the second fixed part are respectively located on both ends of the cuff; a first fixed position is between the pull ring and the second fixed part; and the first fixed part and the second fixed part can form velcro or other hook and loop connection.

The present disclosure has the beneficial effects: providing tight inside layer and a loose outside layer is achieved by the combination of the elastic liner and the cuff. When worn on an upper arm, the elastic liner has an elastic deformation and consequently tightens around the upper arm so as to provide slip resistance, and the cuff will not slip down even when fastened somewhat loosely when positioned on the upper arm. Therefore, the feeling of constraint from the cuff is reduced significantly, the comfort is improved and the cuff is suitable for long wear. During long-time use, it may not generate symptoms of swelling, bruising, etc. in the position of the upper arm of a patient where the cuff is fastened.

DETAILED DESCRIPTION

Figure 1:
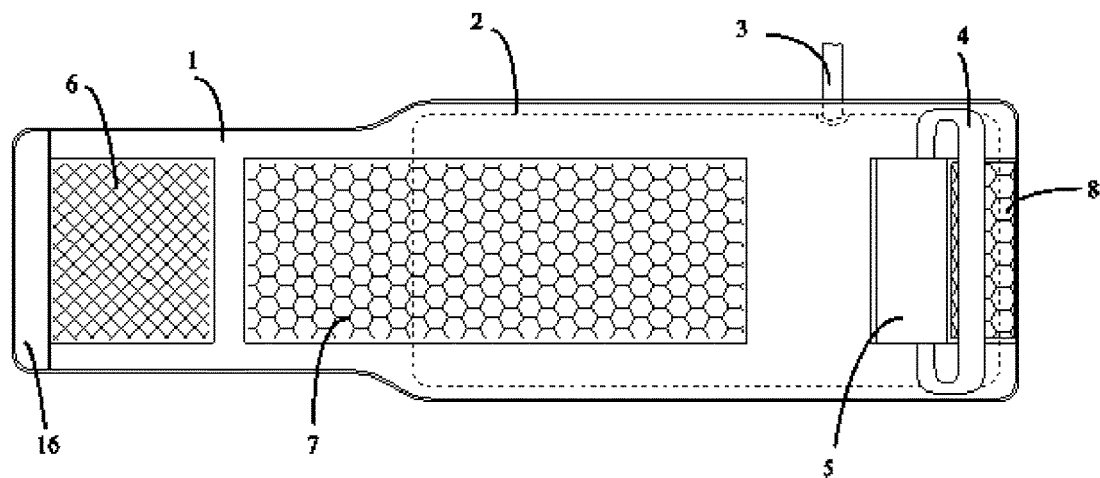
FIG. 1 is a schematic diagram of a front side of a cuff of a blood pressure cuff assembly of the present disclosure.

As shown in FIGS. 1 to 13, the blood pressure cuff assembly comprises a band-shaped cuff 14 having a cuff length and a band-shaped liner 15 having a liner length. The cuff 14 has a front side and a reverse side. When the cuff 14 is worn around a target position of a patient, the front side faces outward and the reverse side faces inward. The liner 15 is made of elastic material. When strained, the liner 15 can have an elastic deformation to extend in a lengthwise direction. The liner 15 is connected to the reverse side of the cuff 14.

When worn, the cuff 14 and the liner 15 connected therewith wrap around a target position 17, and the liner 15 extends to tighten around the target position, but the cuff 14 is loose. The whole cuff assembly stays positioned around the target position 17 by means of frictional force between the tightened liner and the target position.

After wrapping the blood pressure cuff assembly around the target position 17, an additional element is used for fixing the cuff 14 to prevent the cuff and the liner from being loosened. The element may be a fibula. As shown, a first fixed part and a second fixed part in separable connection can also be arranged on the cuff 14. After wrapping, the first fixed part and the second fixed part are connected to achieve fixation of the cuff.

As shown in FIGS. 1 to 13, the blood pressure cuff assembly comprises a band-shaped cuff 14 and a band-shaped liner 15. The cuff 14 is includes a first connection part 8 and a second connection part 9 spaced in a lengthwise direction, and the liner 15 correspondingly includes a third connection part 13 and a fourth connection part 12.

In a natural flat state, a spacing between the first connection part 8 and the second connection part 9 may be greater than a spacing between the third connection part 13 and the fourth connection part 12; the first connection part 8 and the third connection part 13 are in separable connection. The second connection part 9 and the fourth connection part 12 are in separable connection such that the length of the part of the liner 15 between the third and the fourth connection parts is less than the length of the part of the cuff 14 between the first and the second connection parts, and is also less than the total length of the cuff.

After the cuff 14 and the liner 15 are connected, the liner 15 may be straight, while the cuff 14 is slightly arched. After the whole cuff assembly is worn around the target position 17, a cuff guidance end 16 is pulled. Because the liner 15 is short, the liner 15 is first tightened. Thus, when the cuff 14 is in a loose state, the liner 15 may be tightened around the target position 17.

In one embodiment, the separable connection of the cuff and the liner may be a button connection, snapper connection, zipper connection, thread connection, tie connection or self-seal connection. Button connection means that between paired connection parts, one is provided with a button hole and the other one is provided with a button. Snapper connection means that between paired connection parts, one is provided with a male snapper and the other one is provided with a female snapper. Zipper connection means that between paired connection parts: one part includes a first row of teeth distributed along a length of the cuff or liner; the other part includes a second row of teeth distributed along a length of the liner or cuff; and a slide block of a zipper is arranged on one of the two parts. Thread connection means that paired connection parts are sewn together. Tie connection means that paired connection parts are tied together with a rope. Self-seal connection is like an existing self-seal structure applied to a packaging bag.

In one embodiment, above various modes of separable connection may be regarded as no length on the connection parts.

In another embodiment, the cuff may be provided with a first fixed part and a second fixed part in separable connection, and the first and the second fixed parts are used to fix the cuff to prevent the cuff and the liner from being loosened about the target position. Separable connection of the first and the second fixed parts may be similar to the separable connection as described above with respect to the connection parts.

As shown in FIGS. 1 to 16, the cuff assembly comprises a cuff 14 and an elastic liner 15. The cuff 14 has a first connection part 8 and a second connection part 9, and the liner 15 has a third connection part 13 and a fourth connection part 12. The first connection part 8 and the third connection part 13 have a velcro connection, and the second connection part 9 and the fourth connection part 12 have a velcro connection.

Velcro consists of a plurality of velcro loop portions and velcro hook portions. The velcro loop portions and the velcro hook portions have certain lengths. A maximum cuff spacing a2 and a minimum cuff spacing a1 exist between the first connection part 8 and the second connection part 9, and a maximum liner spacing b2 and a minimum liner spacing b1 exist between the third connection part 13 and the fourth connection part 12.

Figure 14:
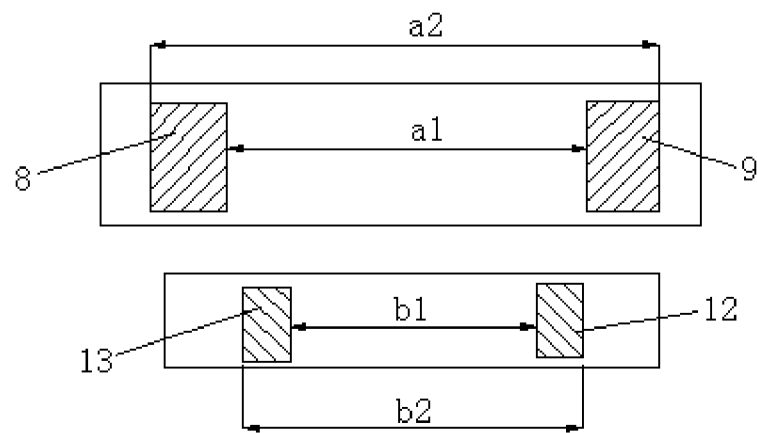
FIGS. 14 to 16 are schematic diagrams reflecting three position relationships of corresponding connection parts between a cuff and a liner respectively.
Figure 15:
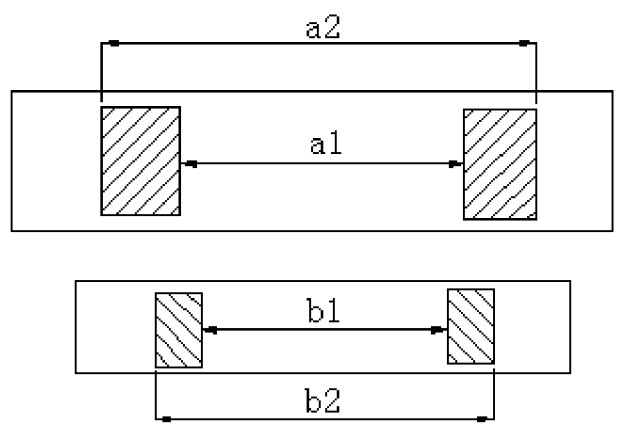
Figure 16:
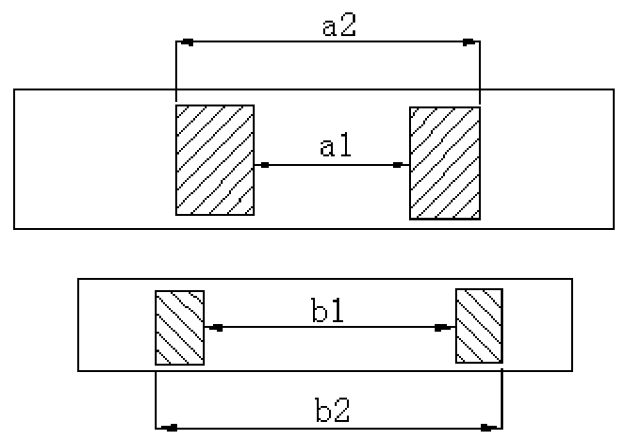

To tighten the liner around the target position while keeping the cuff loose when worn by a patient, the maximum cuff spacing a2 should be at least greater than the minimum liner spacing b1, as shown in FIG. 14 to FIG. 16.

As shown in FIG. 14, the minimum cuff spacing a1 is greater than the minimum liner spacing b1 and the maximum cuff spacing a2 is greater than the maximum liner spacing b2 so as to ensure that the liner is tight around the target position while the cuff is loose when worn on a patient after the cuff and the liner are in velcro connection.

As shown in FIG. 15, the minimum cuff spacing a1 is greater than the minimum liner spacing b1 and is less than the maximum liner spacing b2 so as to ensure that the liner is tight while the cuff is loose when worn on a patient by setting the adhesion initial position and the adhesion length of the liner and the cuff. The velcro loops and the velcro hooks start to adhere from the adhesion initial position. The adhesion length means a length of an adhesion part between the velcro loops and the velcro hooks.

As shown in FIG. 16, the maximum cuff spacing a2 is greater than the minimum liner spacing b1 and is less than the maximum liner spacing b2 so as to ensure that the liner is tight while the cuff is loose when worn on a patient by setting the adhesion initial position and the adhesion length of the liner and the cuff. For example, the outer side of the first connection part and the outer side of the second connection part are respectively connected with the inner side of the second connection part and the inner side of the fourth connection part, thereby allowing the liner to be tight while the cuff is loose.

As shown in FIGS. 1 to 13, the cuff assembly comprises a cuff 14 and an elastic liner 15.
i. The front side of the cuff, which may also be referred to as the outer side of the cuff, shall face outward when worn on an arm of a patient, as shown in FIG. 1. The front side of the cuff comprises an outer wrapping cloth 1 of the cuff, a pull ring 4, a pull ring fixing cloth, a velcro hook portion 6, a velcro loop portion 7 and a velcro loop portion 8, wherein the pull ring fixing cloth 5 penetrates through the pull ring 4 and is sewn on the outer wrapping cloth 1, so as to fix the pull ring 4 to the front side of the cuff. The pull ring 4 may be made of metal, plastic, or any other suitable material, and allows the patient to put on the blood pressure cuff without assistance from others. If no pull ring is arranged, the cuff must be fastened to the patient by doctors, nurses or others, and the patient may not be able to fasten the cuff easily without assistance. However, after the pull ring is arranged, the cuff guidance end 16 can penetrate through the pull ring 4 so that a cylindrical cuff ring is formed on the cuff and fastened to an arm of the patient. Then the guidance end 16 is pulled to tighten the cuff ring, and the velcro hook portion 6 is stuck to the velcro loop portion 7 to fix the cuff so as to prevent the cuff from being loosened.

Figure 2:
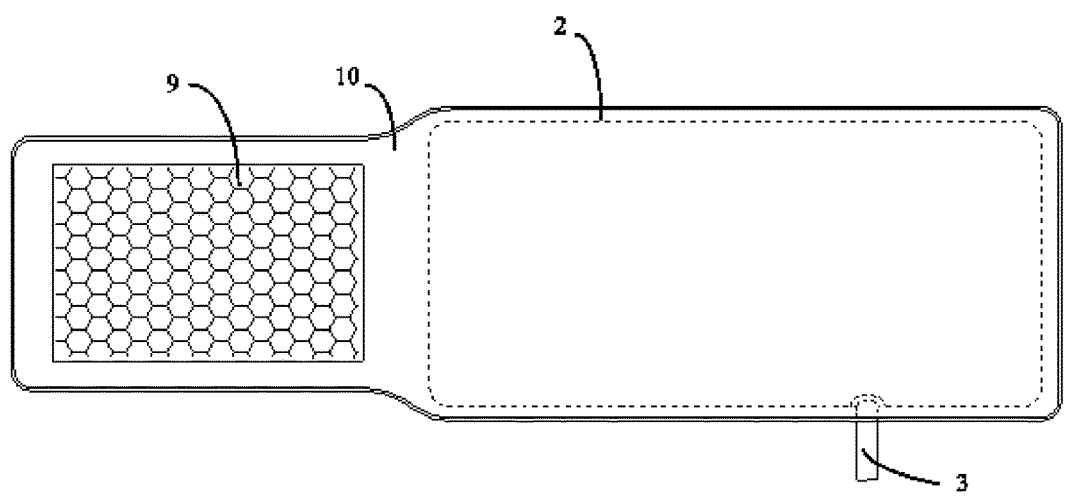
FIG. 2 is a schematic diagram of a reverse side of a cuff of a blood pressure cuff assembly of the present disclosure.

The reverse side of the cuff, which may also be referred to as the inner side of the cuff, may be close to the arm of the patient when worn on the arm of the patient, as shown in FIG. 2. The reverse side of the cuff comprises inner wrapping cloth 10 of the cuff and a velcro loop portion 9, wherein the inner wrapping cloth 10 may be in direct contact with skin of the patient.

An airbag 2 and an air duct 3 are arranged between the outer wrapping cloth 1 and the inner wrapping cloth 10 of the cuff. After the cuff is fixed, the air duct 3 is connected to a blood pressure measuring device. During measurement, the airbag 2 is inflated by the air duct 3. When air pressure reaches a certain value, the airbag 2 is deflated. The blood pressure measuring device calculates the blood pressure of the patient by detecting a real-time change of the air pressure in the airbag 2.

Figure 3:
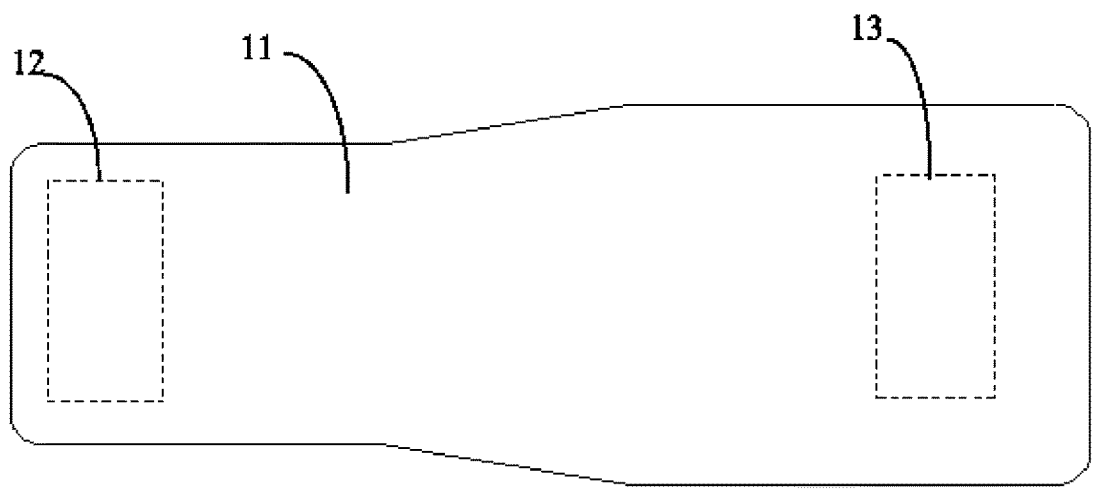
FIG. 3 is a schematic diagram of a reverse side of a liner of a blood pressure cuff assembly of the present disclosure.
Figure 4:
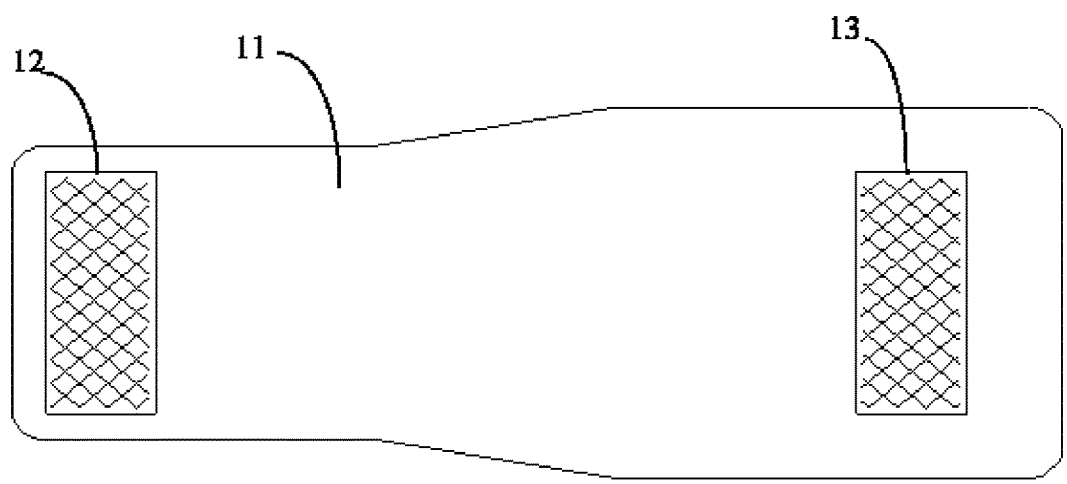
FIG. 4 is a schematic diagram of a front side of a liner of a blood pressure cuff assembly of the present disclosure.

The composition of the elastic liner is shown in FIGS. 3 and 4.

The elastic liner comprises lining cloth 11 of the liner, a velcro hook portion 12 and a velcro hook portion 13, wherein the lining cloth 11 of the liner may be selected from such fabrics as lycra, nylon, etc. providing elasticity, permeability and comfort.

FIG. 3 shows a reverse side of the elastic liner positioned close to the skin. FIG. 4 shows a front side of the elastic liner secured to the cuff 14 through the velcro hook portion 12 and the velcro hook portion 13.

The fastening process of the blood pressure cuff assembly is shown in FIGS. 5 to 13.

Figure 5:
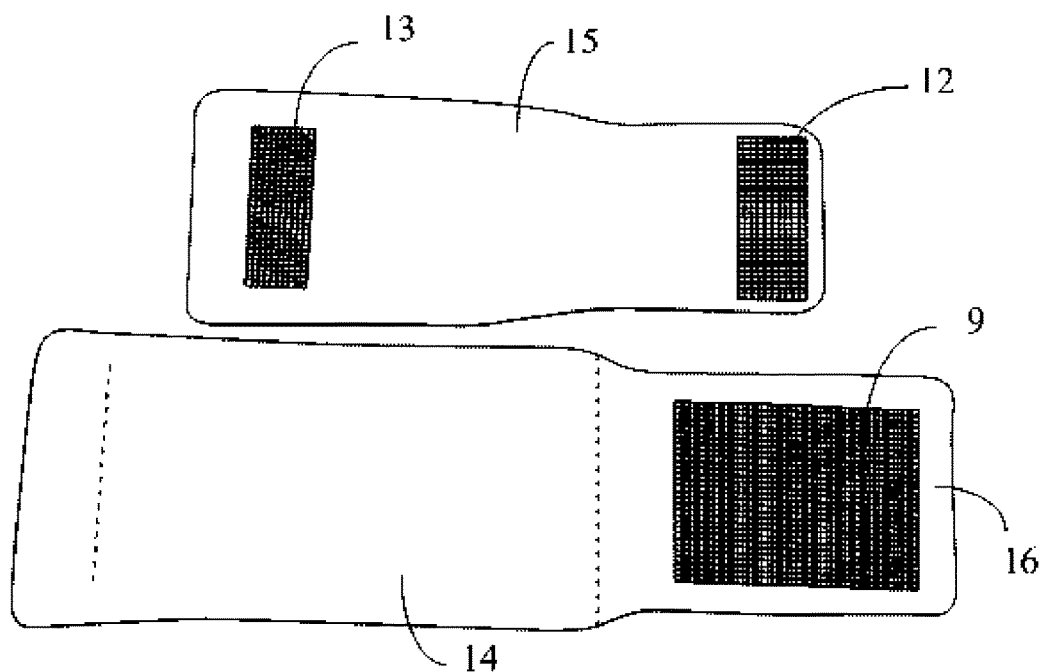
FIGS. 5 to 13 are schematic diagrams of a wearing process of a blood pressure cuff assembly of the present disclosure.

The cuff 14 and the elastic liner 15 are placed flatly on a table, as shown in FIG. 5, with the reverse side of the cuff 14 facing upward and the front side facing downward.

Figure 6:
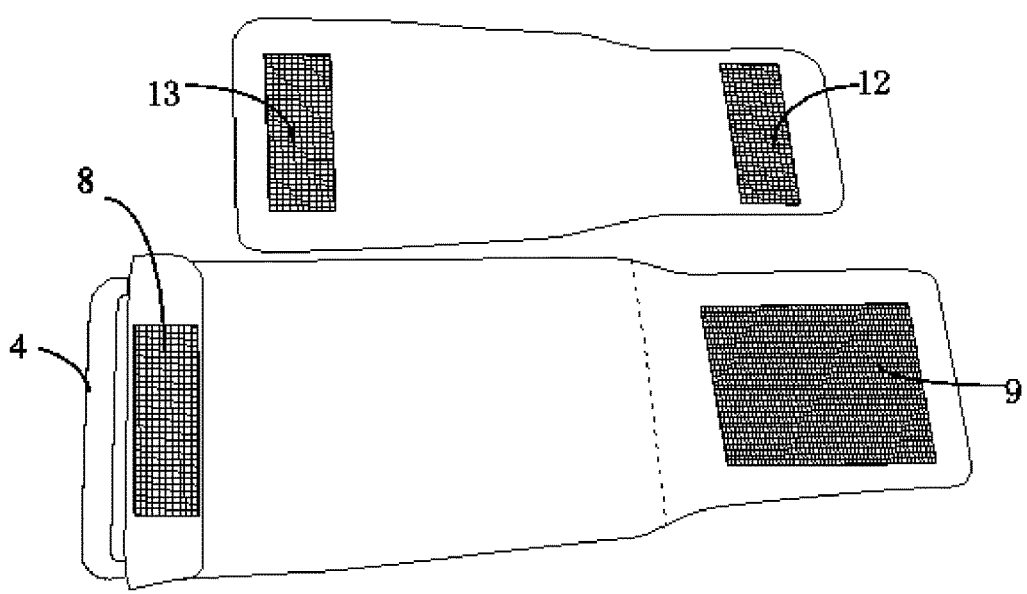

At this moment, the pull ring 4 side of the cuff is turned up and bent so that the velcro loop portion 8 is exposed and faces upward. Even when the velcro loop portion 8 and the velcro hook portion 9 face the front side of the liner 15, as shown in FIG. 6, the pull ring 4 may also be exposed.

Figure 7:
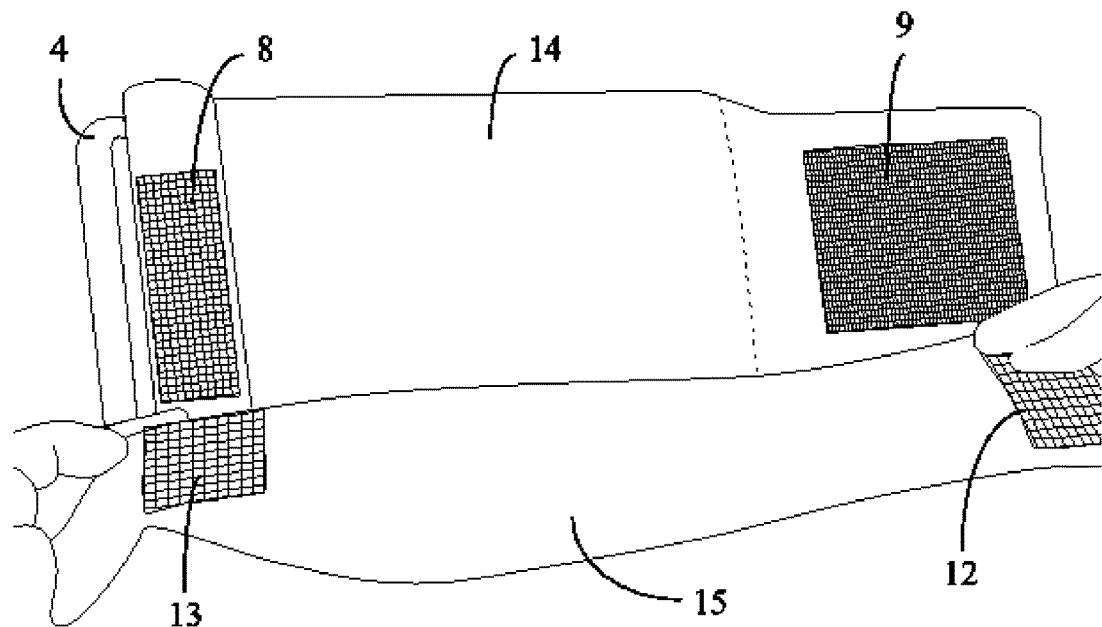
Figure 8:
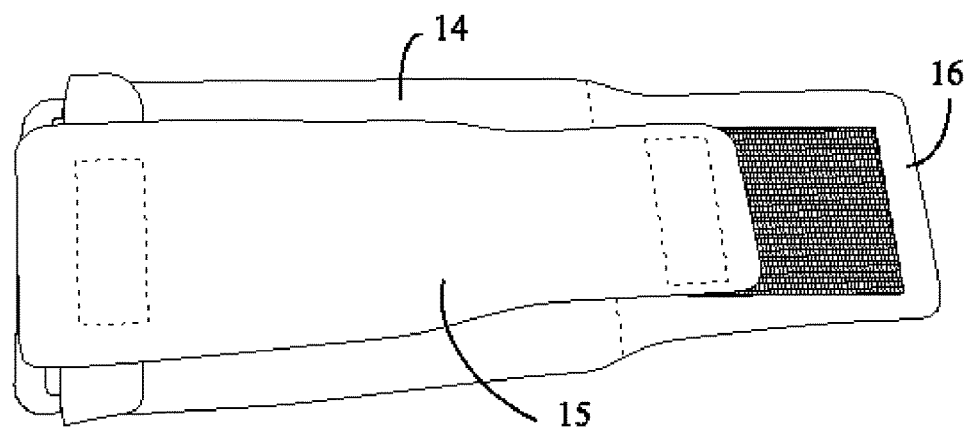

As shown in FIG. 7, the elastic liner 15 is taken with both hands. The front side of the liner faces downward opposite to the reverse side of the reusable cuff 14, as shown in FIG. 7. The velcro hook portion 13 is stuck to the velcro loop portion 8, and the velcro hook portion 12 is stuck to the velcro loop portion 9. The elastic liner 15 is combined with the cuff 14 with a velcro connection, as shown in FIG. 8.

Figure 9:
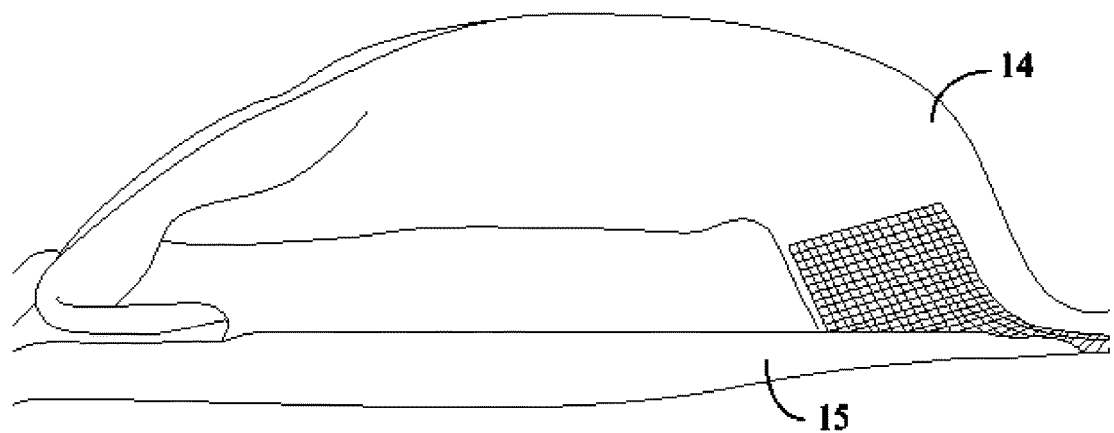

Because the length of the elastic liner 15 in a natural flat state (unstretched state) is slightly shorter than the distance between the velcro loop portion 8 and the velcro loop portion 9 on the cuff 14 (in other words, a distance between the velcro loop portion 13 and the velcro hook portion 12 on the liner 15 is less than the distance between the velcro loop portion 8 and the velcro loop portion 9 on the cuff), after the liner 15 and the cuff 14 are combined together, the liner 15 is straight while the cuff 14 is arched when viewed from a side surface, as shown in FIG. 9.

Figure 10:
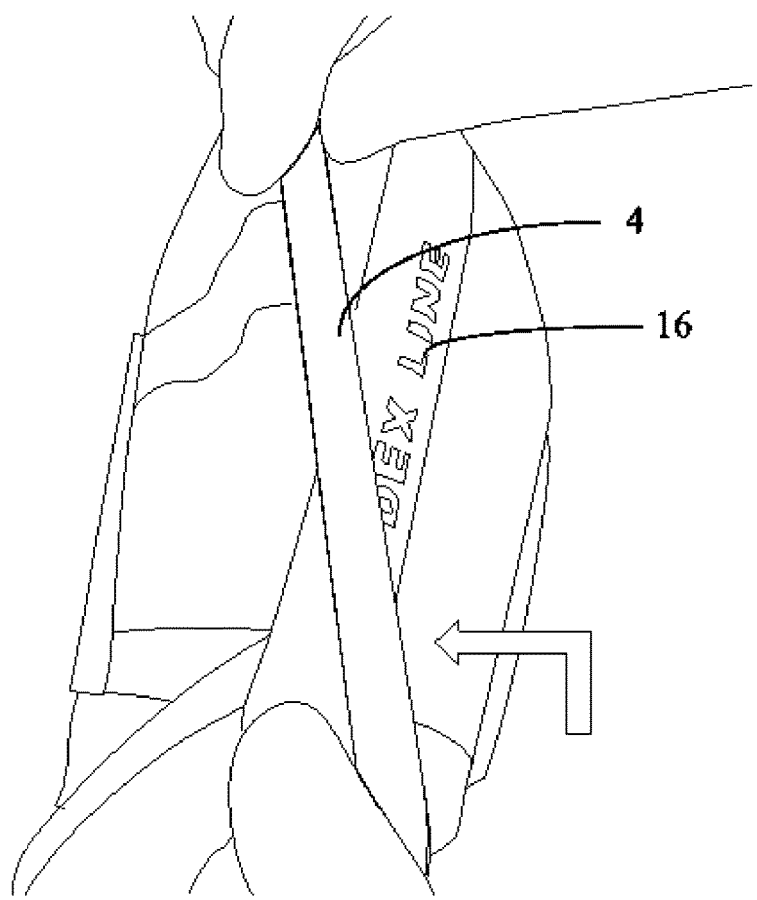
Figure 11:
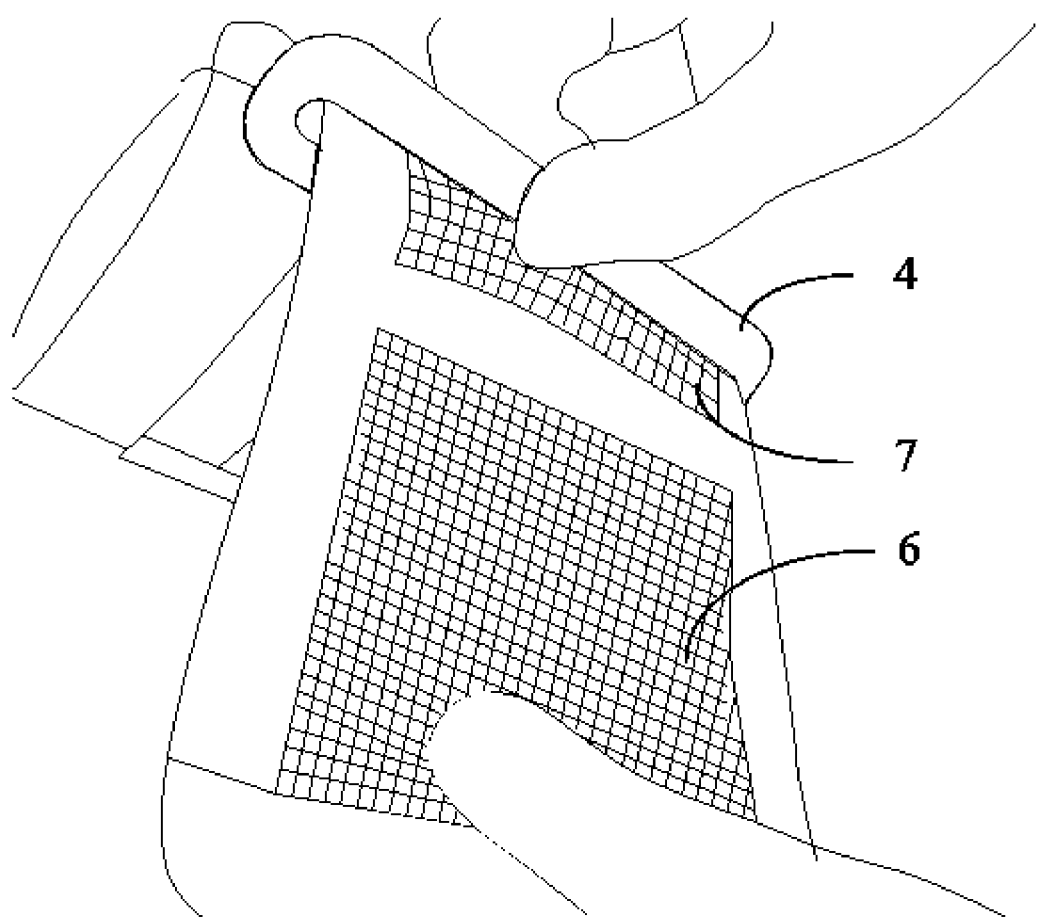

The cuff guidance end 16 together with the stuck elastic liner penetrates through the pull ring 4, as shown in FIG. 10 and FIG. 11, so that a cylinder shape is formed by the cuff and the elastic liner, wherein the inner elastic liner forms an elastic cylinder with a smaller diameter due to its relatively shorter length, and the outer cuff forms a larger cylinder and may not generate an elastic deformation.

Figure 12:
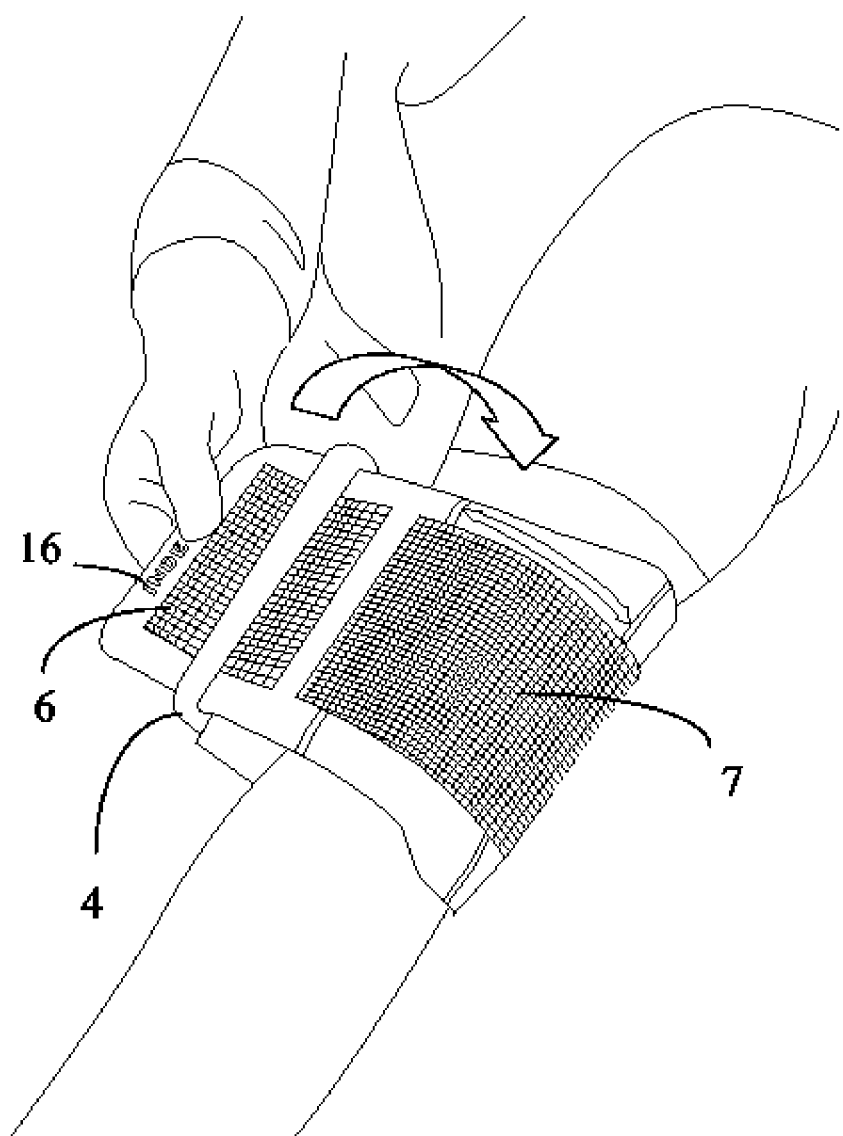

At this moment, the cylindrical cuff and liner are sheathed into an upper arm of the patient together, as shown in FIG. 12, and the cuff guidance end 16 is pulled in a reverse direction as shown by the arrow to tighten the cuff and the elastic liner together. The elastic liner 15 is first tightened due to its shorter length. Thus, even though the cuff 14 is loose, the elastic liner is tightened around the arm so that the whole cuff may stay in place. Because the elastic liner is made of high-elasticity material such as lycra, for example, the elastic liner may not generate a feeling of restraint on the upper arm of the patient after tightened.

Figure 13:
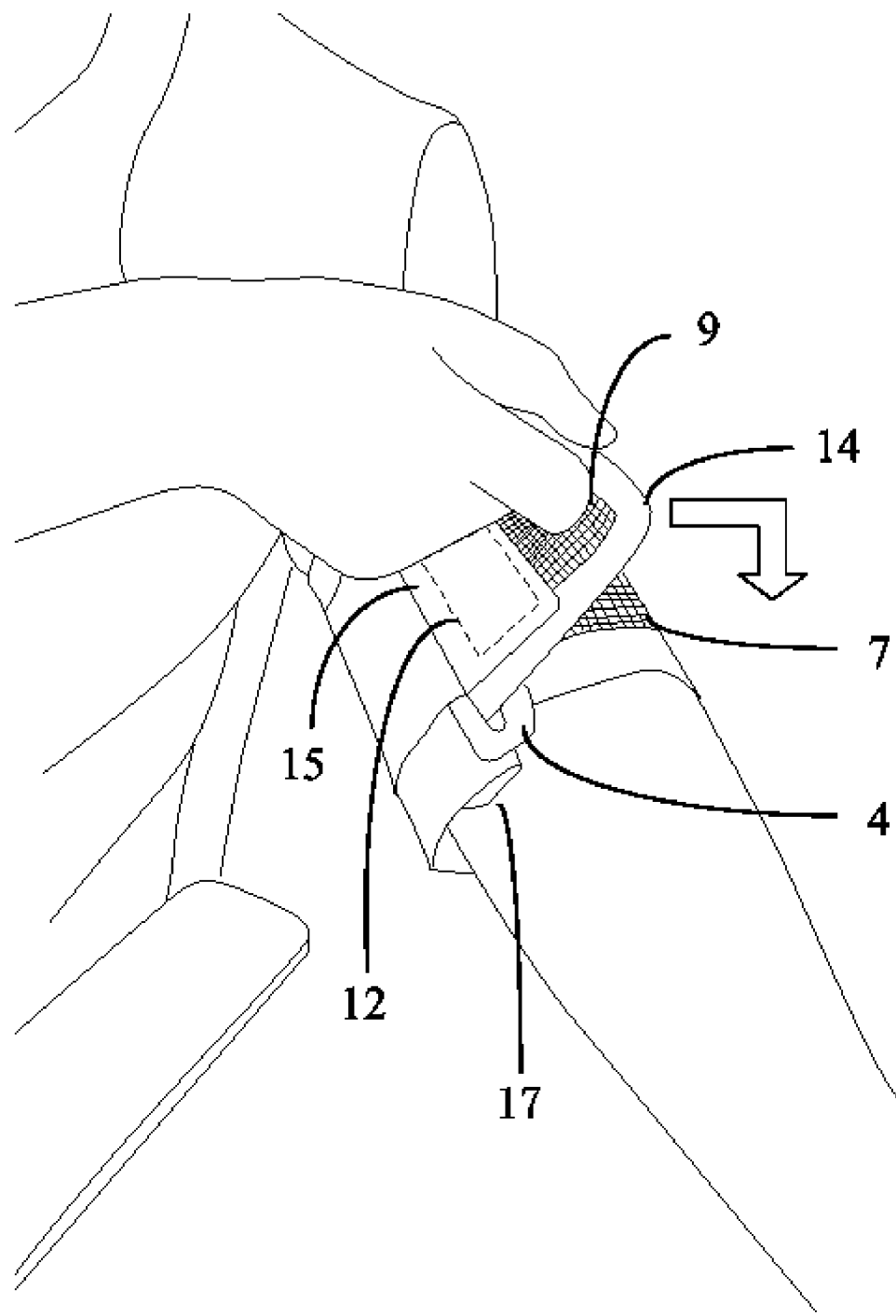

After the tightness of the cuff is appropriately adjusted, as shown in FIG. 13, the elastic liner 15 is in a tight state and the cuff 14 may be appropriately loosened. At this moment, the velcro hook portion 6 and the velcro loop portion 7 are stuck together in accordance with the direction of the arrow so as to finish the fixation of the cuff. After the cuff is fixed, because the velcro hook portion 12 on the liner 15 and the velcro loop portion 9 on the cuff 14 are stuck together, part of the liner 15 is pulled through the pull ring 4 by the cuff guidance end 16 and is exposed.

The blood pressure cuff assembly comprises a cuff and a liner. The cuff has a front side and a reverse side, and the liner is in separable connection with the reverse side of the cuff. When the cuff assembly is worn around the target position, the liner and the cuff wrap around the target position, and the liner is tight while the cuff is loose. Generally, the liner and the cuff wrap around the target position with at least one circle. After finishing wrapping, to prevent the cuff and the liner from being loosened about the target position, an additional element is used for fixing the cuff (in other words, a first fixed part and a second fixed part in separable connection may be arranged on the cuff for fixing the cuff). The first fixed part and the second fixed part can form a velcro connection, wherein one of the two is a velcro hook portion and the other one of the two is a velcro loop portion and the loop portion and the hook portion may be respectively arranged on the front side and the reverse side of the cuff. The loop and the hook may be simultaneously arranged on the front side of the cuff. Meanwhile, by installing the pull ring, the cuff guidance end can reversely wrap around the pull ring and then the loop portion and the hook portion are stuck together.

The blood pressure cuff assembly may be applied to an ambulatory blood pressure monitor.

The blood pressure cuff comprises a cuff and a liner connected therewith, and has the following advantages:

1) Providing a tight inside layer and loose outside layer is achieved by the combination of the elastic liner and the cuff. That is, after being placed about a target position (e.g., upper arm), the elastic liner 15 can fix the cuff to the target position to provide a slip resistance effect, and the cuff will not slip down even if fastened a bit loosely. Therefore, the feeling of constraint from the cuff is reduced significantly, the comfort is improved, and the cuff is suitable for wearing for long periods of time. During long-time use, it may not generate symptoms of swelling, bruising, etc. in the position of the upper arm of a patient where the cuff is tied.

2) After the elastic liner is used, a certain gap may exist between the outer cuff and the liner, thereby improving permeability and reducing the tendency of the cuff to become dirty and odorous due to perspiration.

3) Because the elastic liner may be designed to be disposable and a cuff liner is replaced after a patient is measured, measurement is more hygienic and cross infection of dermatopathy, etc. may be avoided.

In addition, if the elastic liner is not used, the individual use of the cuff may not be influenced.

The above contents are further detailed descriptions of the present disclosure in combination with the specific embodiments. However, the specific embodiments of the present disclosure are not limited to these descriptions. For those of ordinary skill in the art to which the present disclosure belongs, several simple deductions or replacements may be made without departing from the conception of the present disclosure.

The invention claimed is:

1. A blood pressure cuff assembly comprising: a cuff; and an elastic liner, wherein the liner is in a separable connection with a reverse side of the cuff;
    wherein, in a natural flat state, the cuff has a first connection part and a second connection part spaced in a lengthwise direction, and the liner has a third connection part and a fourth connection part spaced in a lengthwise direction, the first connection part and the third connection part is capable of forming a first separable connection, and the second connection part and the fourth connection part forming a second separable connection;
    wherein a spacing between the first connection part and the second connection part is greater than a spacing between the third connection part and the fourth connection part.

2. The blood pressure cuff assembly of claim 1, wherein the first separable connection and the second separable connection comprise at least one of a zipper connection, a button connection, a snap connection, a thread connection, a tie connection and a self-seal connection.

3. The blood pressure cuff assembly of claim 1, wherein a first fixed part is arranged on the reverse side of the cuff, and a second fixed part is arranged on a front side of the cuff, the first fixed part and the second fixed part forming a hook-and-loop connection.

4. The blood pressure cuff assembly of claim 1, wherein a pull ring, a first fixed part, and a second fixed part are arranged on a front side of the cuff; wherein the pull ring and the second fixed part are respectively located on each end of the cuff; the first fixed part is located between the pull ring and the second fixed part; the first fixed part and the second fixed part forming a hook-and-loop connection.

5. A blood pressure cuff assembly, comprising: a cuff; and an elastic liner, wherein the liner is in a separable connection with the reverse side of the cuff;
    wherein in a natural flat state, the cuff has a first connection part and a second connection part spaced in a lengthwise direction, and the liner has a third connection part and a fourth connection part spaced in a lengthwise direction;
    wherein the first connection part and the third connection part form a first hook-and-loop connection, and the second connection part and the fourth connection part form a second hook-and-loop connection;
    wherein a maximum cuff spacing and a minimum cuff spacing exist between the first connection part and the second connection part, and a maximum liner spacing and a minimum liner spacing exist between the third connection part and the fourth connection part, the maximum cuff spacing being greater than the minimum liner spacing.

6. The blood pressure cuff assembly of claim 5, wherein the minimum liner spacing is less than the minimum cuff spacing.

7. The blood pressure cuff assembly of claim 5, wherein the maximum liner spacing is less than the maximum cuff spacing.

8. The blood pressure cuff assembly of claim 5, wherein a first fixed part is arranged on the reverse side of the cuff; a second fixed part is arranged on a front side of the cuff; and the first fixed part and the second fixed part form a hook-and-loop connection.

9. The blood pressure cuff assembly of claim 5, wherein a pull ring, a first fixed part, and a second fixed part are arranged on a front side of the cuff; the pull ring and the second fixed part are respectively located on each end of the cuff; the first fixed part is located between the pull ring and the second fixed part; and the first fixed part and the second fixed part form a hook-and-loop connection.

10. A blood pressure cuff for an ambulatory blood pressure monitor, comprising: a hollow cuff; and
    an elastic liner provided on a reverse side of the cuff;
    wherein an airbag is provided in the cuff, a first connection part and a second connection part are provided on the cuff, a third connection part and a fourth connection part are correspondingly provided on the liner, the first connection part is connected with the third connection part, the second connection part is connected with the fourth connection part, when a part of the liner between the third connection part and the fourth connection part is straight, a part of the cuff between the first connection part and the second connection part is arched.

11. The blood pressure cuff assembly of claim 10, wherein the first connection part and the third connection part form a first separable connection, and the second connection part and the fourth connection part form a second separable connection.

12. The blood pressure cuff assembly of claim 10, wherein the first connection part and the third connection part form a hook-and-loop connection, and the second connection part and the fourth connection part form a hook-and-loop connection.

13. The blood pressure cuff assembly of claim 10, wherein a first fixed part is arranged on the reverse side of the cuff; a second fixed part is arranged on a front side of the cuff; and the first fixed part and the second fixed part form a hook-and-loop connection.

14. The blood pressure cuff assembly of claim 10, wherein a pull ring, a first fixed part, and a second fixed part are arranged on a front side of the cuff; the pull ring and the second fixed part are respectively located on each end of the cuff; the first fixed part is located between the pull ring and the second fixed part; and the first fixed part and the second fixed part form a hook-and-loop connection.

* * * * *